United States Patent
Wong et al.

(10) Patent No.: US 10,349,925 B2
(45) Date of Patent: Jul. 16, 2019

(54) METHOD FOR PROGRAMMING FOOT PEDAL SETTINGS AND CONTROLLING PERFORMANCE THROUGH FOOT PEDAL VARIATION

(75) Inventors: Wayne S. Wong, Irvine, CA (US); Michael J. Claus, Newport Coast, CA (US); Timothy Hunter, Irvine, CA (US); Abraham Hajishah, Irvine, CA (US); Jeremy T. Links, Tustin, CA (US)

(73) Assignee: Johnson & Johnson Surgical Vision, Inc., Santa Ana, CA (US)

( * ) Notice: Subject to any disclaimer, the term of this patent is extended or adjusted under 35 U.S.C. 154(b) by 36 days.

(21) Appl. No.: 12/613,591

(22) Filed: Nov. 6, 2009

(65) Prior Publication Data
US 2011/0092887 A1    Apr. 21, 2011

Related U.S. Application Data

(60) Provisional application No. 61/112,517, filed on Nov. 7, 2008.

(51) Int. Cl.
*A61B 17/20* (2006.01)
*G05G 1/30* (2008.04)
(Continued)

(52) U.S. Cl.
CPC .............. *A61B 17/00* (2013.01); *A61B 90/98* (2016.02); *G05G 1/445* (2013.01);
(Continued)

(58) Field of Classification Search
CPC ................ A61B 17/00; A61B 90/98; A61B 2017/00977; A61B 2017/00225;
(Continued)

(56) References Cited

U.S. PATENT DOCUMENTS

| | | | |
|---|---|---|---|
| 1,848,024 | A | 3/1932 | Owen |
| 2,123,781 | A | 7/1938 | Huber |

(Continued)

FOREIGN PATENT DOCUMENTS

| | | |
|---|---|---|
| AU | 2006235983 A1 | 5/2007 |
| DE | 3826414 A1 | 2/1989 |

(Continued)

OTHER PUBLICATIONS

Merritt R, "Wireless nets starting to link medical gear", Published on Jan. 7, 2004, Published at Embedded.com URL: http://embedded.com/news/ennbeddedindustry/17200577? (Year: 2004).*

(Continued)

*Primary Examiner* — Chun Cao
*Assistant Examiner* — Alan Chu
(74) *Attorney, Agent, or Firm* — Johnson & Johnson Surgical Vision, Inc.

(57) ABSTRACT

The present invention pertains to programming a foot pedal and switches located therewith that is used with a medical device and/or medical device system. A user may select any switch or directional movement available on the foot pedal for programming by activating the switch and/or moving a treadle located on the foot pedal or by selecting a foot pedal feature on a display. The programming options available for the selected switch or directional movement are displayed on the display screen. Using the foot pedal, the display screen, voice command or combinations thereof, the user can navigate through different options to select one or more options and confirm the chosen option(s) for the particular switch or directional movement. The control and feel of the movement of the treadle and/or switch provides the user with the ability to program custom settings that suit the user's foot position(s) and/or particular style of surgery.

34 Claims, 9 Drawing Sheets

(51) Int. Cl.
*A61B 17/00* (2006.01)
*G05G 1/445* (2008.04)
*A61B 90/98* (2016.01)
*A61F 9/007* (2006.01)

(52) U.S. Cl.
CPC .............. *A61B 2017/00199* (2013.01); *A61B 2017/00203* (2013.01); *A61B 2017/00225* (2013.01); *A61B 2017/00973* (2013.01); *A61B 2017/00977* (2013.01); *A61F 9/00745* (2013.01); *Y10T 74/20528* (2015.01)

(58) Field of Classification Search
CPC ........... A61B 2017/00203; A61B 2017/00199; A61B 2017/00973; G05G 1/445; Y10T 74/20528; A61F 9/00745
USPC .................. 433/113; 351/167; 600/126, 135; 700/13
See application file for complete search history.

(56) References Cited

U.S. PATENT DOCUMENTS

| | | |
|---|---|---|
| 2,990,616 A | 7/1961 | Balamuth et al. |
| 3,076,904 A | 2/1963 | Klesattel et al. |
| 3,116,697 A | 1/1964 | Theodore |
| 3,439,680 A * | 4/1969 | Thomas, Jr. ................... 606/24 |
| 3,526,219 A | 9/1970 | Balamuth |
| 3,781,142 A | 12/1973 | Zweig |
| 3,857,387 A | 12/1974 | Shock |
| 4,017,828 A | 4/1977 | Watanabe et al. |
| 4,037,491 A | 7/1977 | Newbold |
| 4,189,286 A | 2/1980 | Murry et al. |
| 4,193,004 A | 3/1980 | Lobdell et al. |
| 4,247,784 A | 1/1981 | Henry |
| 4,276,023 A | 6/1981 | Phillips et al. |
| 4,537,561 A | 8/1985 | Xanthopoulos |
| 4,564,342 A | 1/1986 | Weber et al. |
| 4,590,934 A * | 5/1986 | Malis et al. ................... 606/37 |
| 4,662,829 A | 5/1987 | Nehring |
| 4,665,621 A * | 5/1987 | Ackerman et al. ............. 33/513 |
| 4,706,687 A * | 11/1987 | Rogers et al. ................ 600/565 |
| 4,757,814 A | 7/1988 | Wang et al. |
| 4,758,220 A | 7/1988 | Sundblom et al. |
| 4,772,263 A | 9/1988 | Dorman et al. |
| 4,773,897 A | 9/1988 | Scheller et al. |
| 4,818,186 A | 4/1989 | Pastrone et al. |
| 4,837,857 A | 6/1989 | Scheller et al. |
| 4,920,336 A | 4/1990 | Meijer |
| 4,921,477 A | 5/1990 | Davis |
| 4,933,843 A * | 6/1990 | Scheller et al. ................ 604/22 |
| 4,941,518 A | 7/1990 | Williams et al. |
| 4,954,960 A | 9/1990 | Lo et al. |
| 4,961,424 A | 10/1990 | Kubota et al. |
| 4,965,417 A | 10/1990 | Massie |
| 4,983,901 A | 1/1991 | Lehmer |
| 4,998,972 A * | 3/1991 | Chin et al. .................... 600/109 |
| 5,006,110 A | 4/1991 | Garrison et al. |
| 5,020,535 A | 6/1991 | Parker et al. |
| 5,026,387 A | 6/1991 | Thomas |
| 5,032,939 A | 7/1991 | Mihara et al. |
| 5,039,973 A | 8/1991 | Carballo |
| 5,091,656 A | 2/1992 | Gahn |
| 5,108,367 A | 4/1992 | Epstein et al. |
| 5,110,270 A | 5/1992 | Morrick |
| 5,125,891 A | 6/1992 | Hossain et al. |
| 5,160,317 A | 11/1992 | Costin |
| 5,195,960 A | 3/1993 | Hossain et al. |
| 5,195,961 A | 3/1993 | Takahashi et al. |
| 5,195,971 A | 3/1993 | Sirhan |
| 5,230,614 A | 7/1993 | Zanger et al. |
| 5,242,404 A | 9/1993 | Conley et al. |
| 5,249,121 A * | 9/1993 | Baum et al. ................... 606/1 |
| 5,268,624 A | 12/1993 | Zanger |
| 5,271,379 A * | 12/1993 | Phan et al. ................... 600/104 |
| 5,282,787 A | 2/1994 | Wortrich |
| 5,323,543 A | 6/1994 | Steen et al. |
| 5,342,293 A | 8/1994 | Zanger |
| 5,350,357 A | 9/1994 | Kamen et al. |
| 5,351,676 A * | 10/1994 | Putman ...................... 600/117 |
| 5,388,569 A | 2/1995 | Kepley |
| 5,454,783 A | 10/1995 | Grieshaber et al. |
| 5,464,391 A | 11/1995 | Devale |
| 5,470,211 A | 11/1995 | Knott et al. |
| 5,470,312 A | 11/1995 | Zanger et al. |
| 5,499,969 A | 3/1996 | Beuchat et al. |
| 5,520,652 A | 5/1996 | Peterson |
| 5,533,976 A | 7/1996 | Zaleski et al. |
| 5,549,461 A | 8/1996 | Newland |
| 5,554,894 A | 9/1996 | Sepielli |
| 5,561,575 A | 10/1996 | Eways |
| 5,569,188 A | 10/1996 | Mackool |
| 5,580,347 A * | 12/1996 | Reimels ...................... 604/30 |
| 5,591,127 A | 1/1997 | Barwick, Jr. et al. |
| 5,653,887 A | 8/1997 | Wahl et al. |
| 5,657,000 A | 8/1997 | Ellingboe |
| 5,676,530 A | 10/1997 | Nazarifar |
| 5,676,649 A | 10/1997 | Boukhny et al. |
| 5,676,650 A | 10/1997 | Grieshaber et al. |
| 5,693,020 A | 12/1997 | Rauh |
| 5,697,898 A | 12/1997 | Devine |
| 5,697,910 A | 12/1997 | Cole et al. |
| 5,700,240 A | 12/1997 | Barwick, Jr. et al. |
| 5,724,264 A * | 3/1998 | Rosenberg et al. ............ 702/152 |
| 5,728,130 A | 3/1998 | Ishikawa et al. |
| 5,733,256 A | 3/1998 | Costin |
| 5,745,647 A | 4/1998 | Krause |
| 5,746,713 A | 5/1998 | Hood et al. |
| 5,747,824 A | 5/1998 | Jung et al. |
| 5,777,602 A * | 7/1998 | Schaller ................ G16H 40/63 345/157 |
| 5,805,998 A | 9/1998 | Kodama |
| 5,807,075 A | 9/1998 | Jacobsen et al. |
| 5,810,766 A | 9/1998 | Barnitz et al. |
| 5,830,176 A | 11/1998 | Mackool |
| 5,843,109 A | 12/1998 | Mehta et al. |
| 5,859,642 A * | 1/1999 | Jones ........................... 715/821 |
| 5,871,492 A | 2/1999 | Sorensen |
| 5,879,298 A * | 3/1999 | Drobnitzky et al. ........ 600/407 |
| 5,883,615 A * | 3/1999 | Fago et al. .................... 345/156 |
| 5,899,674 A | 5/1999 | Jung et al. |
| 5,928,257 A | 7/1999 | Kablik et al. |
| 5,938,655 A | 8/1999 | Bisch et al. |
| 5,983,749 A | 11/1999 | Holtorf |
| 6,002,484 A | 12/1999 | Rozema et al. |
| 6,024,428 A | 2/2000 | Uchikata |
| 6,028,387 A | 2/2000 | Boukhny |
| 6,062,829 A | 5/2000 | Ognier |
| 6,077,285 A | 6/2000 | Boukhny |
| 6,086,598 A | 7/2000 | Appelbaum et al. |
| 6,109,895 A | 8/2000 | Ray et al. |
| 6,117,126 A | 9/2000 | Appelbaum et al. |
| 6,139,320 A | 10/2000 | Hahn |
| 6,150,623 A | 11/2000 | Chen |
| 6,159,175 A | 12/2000 | Strukel et al. |
| 6,179,829 B1 * | 1/2001 | Bisch .................. A61C 1/0023 200/51.02 |
| 6,200,287 B1 | 3/2001 | Keller et al. |
| 6,219,032 B1 * | 4/2001 | Rosenberg et al. ........... 345/157 |
| 6,251,113 B1 | 6/2001 | Appelbaum et al. |
| 6,260,434 B1 | 7/2001 | Holtorf |
| 6,360,630 B2 | 3/2002 | Holtorf |
| 6,368,269 B1 * | 4/2002 | Lane .............................. 600/126 |
| 6,411,062 B1 | 6/2002 | Baranowski et al. |
| 6,424,124 B2 | 7/2002 | Ichihara et al. |
| 6,436,072 B1 | 8/2002 | Kullas et al. |
| 6,452,120 B1 | 9/2002 | Chen |
| 6,452,123 B1 | 9/2002 | Chen |
| 6,491,661 B1 | 12/2002 | Boukhny et al. |
| 6,511,454 B1 | 1/2003 | Nakao et al. |
| 6,537,445 B2 | 3/2003 | Muller |
| 6,595,948 B2 | 7/2003 | Suzuki et al. |
| 6,632,214 B2 | 10/2003 | Morgan et al. |
| 6,674,030 B2 | 1/2004 | Chen et al. |

(56) References Cited

U.S. PATENT DOCUMENTS

| | | | |
|---|---|---|---|
| 6,830,555 B2 | 12/2004 | Rockley et al. | |
| 6,852,092 B2 | 2/2005 | Kadziauskas et al. | |
| 6,862,951 B2 | 3/2005 | Peterson et al. | |
| 6,908,451 B2 | 6/2005 | Brody et al. | |
| 6,962,488 B2 | 11/2005 | Davis et al. | |
| 6,962,581 B2 * | 11/2005 | Thoe | 606/1 |
| 6,986,753 B2 | 1/2006 | Bui | |
| 7,011,761 B2 | 3/2006 | Muller | |
| 7,012,203 B2 | 3/2006 | Hanson et al. | |
| 7,070,578 B2 | 7/2006 | Leukanech et al. | |
| 7,073,083 B2 | 7/2006 | Litwin, Jr. et al. | |
| 7,087,049 B2 * | 8/2006 | Nowlin et al. | 606/1 |
| 7,103,344 B2 | 9/2006 | Menard | |
| 7,167,723 B2 | 1/2007 | Zhang | |
| 7,169,123 B2 | 1/2007 | Kadziauskas et al. | |
| 7,236,766 B2 | 6/2007 | Freeburg | |
| 7,236,809 B2 | 6/2007 | Fischedick et al. | |
| 7,242,765 B2 | 7/2007 | Hairston | |
| 7,244,240 B2 | 7/2007 | Nazarifar et al. | |
| 7,289,825 B2 | 10/2007 | Fors et al. | |
| 7,300,264 B2 | 11/2007 | Souza | |
| 7,316,664 B2 | 1/2008 | Kadziauskas et al. | |
| 7,336,976 B2 | 2/2008 | Ito | |
| 7,381,917 B2 | 6/2008 | Dacquay et al. | |
| 7,439,463 B2 | 10/2008 | Brenner et al. | |
| 7,465,285 B2 | 12/2008 | Hutchinson et al. | |
| 7,470,277 B2 | 12/2008 | Finlay et al. | |
| 7,526,038 B2 | 4/2009 | McNamara | |
| 7,591,639 B2 | 9/2009 | Kent | |
| 7,731,484 B2 | 6/2010 | Yamamoto et al. | |
| 7,776,006 B2 | 8/2010 | Childers et al. | |
| 7,811,255 B2 | 10/2010 | Boukhny et al. | |
| 7,883,521 B2 | 2/2011 | Rockley et al. | |
| 7,921,017 B2 * | 4/2011 | Claus et al. | 704/275 |
| 7,967,777 B2 | 6/2011 | Edwards et al. | |
| 8,070,712 B2 | 12/2011 | Muri et al. | |
| 8,075,468 B2 | 12/2011 | Min et al. | |
| 2001/0023331 A1 | 9/2001 | Kanda et al. | |
| 2001/0047166 A1 | 11/2001 | Wuchinich | |
| 2001/0051788 A1 | 12/2001 | Paukovits et al. | |
| 2002/0019215 A1 | 2/2002 | Romans | |
| 2002/0019607 A1 | 2/2002 | Bui | |
| 2002/0045887 A1 * | 4/2002 | DeHoogh et al. | 606/1 |
| 2002/0070840 A1 | 6/2002 | Fischer et al. | |
| 2002/0098859 A1 | 7/2002 | Murata | |
| 2002/0137007 A1 | 9/2002 | Beerstecher | |
| 2002/0179462 A1 | 12/2002 | Silvers | |
| 2002/0183693 A1 | 12/2002 | Peterson et al. | |
| 2003/0028091 A1 * | 2/2003 | Simon et al. | 600/407 |
| 2003/0047434 A1 * | 3/2003 | Hanson et al. | 200/86.5 |
| 2003/0050619 A1 | 3/2003 | Mooijman et al. | |
| 2003/0073980 A1 | 4/2003 | Finlay et al. | |
| 2003/0083016 A1 | 5/2003 | Evans et al. | |
| 2003/0108429 A1 | 6/2003 | Angelini et al. | |
| 2003/0125717 A1 | 7/2003 | Whitman | |
| 2003/0224729 A1 | 12/2003 | Arnold | |
| 2003/0226091 A1 | 12/2003 | Platenberg et al. | |
| 2004/0019313 A1 | 1/2004 | Childers et al. | |
| 2004/0035242 A1 * | 2/2004 | Peterson et al. | 74/560 |
| 2004/0037724 A1 | 2/2004 | Haser et al. | |
| 2004/0068300 A1 | 4/2004 | Kadziauskas et al. | |
| 2004/0092922 A1 | 5/2004 | Kadziauskas et al. | |
| 2004/0193182 A1 | 9/2004 | Yaguchi et al. | |
| 2004/0212344 A1 | 10/2004 | Tamura et al. | |
| 2004/0215127 A1 | 10/2004 | Kadziauskas et al. | |
| 2004/0224641 A1 | 11/2004 | Sinn | |
| 2004/0253129 A1 | 12/2004 | Sorensen et al. | |
| 2005/0039567 A1 | 2/2005 | Peterson et al. | |
| 2005/0054971 A1 | 3/2005 | Steen et al. | |
| 2005/0065462 A1 | 3/2005 | Nazarifar et al. | |
| 2005/0069419 A1 | 3/2005 | Cull et al. | |
| 2005/0070859 A1 | 3/2005 | Cull et al. | |
| 2005/0070871 A1 | 3/2005 | Lawton et al. | |
| 2005/0095153 A1 | 5/2005 | Demers et al. | |
| 2005/0103607 A1 | 5/2005 | Mezhinsky | |
| 2005/0109595 A1 | 5/2005 | Mezhinsky et al. | |
| 2005/0118048 A1 | 6/2005 | Traxinger | |
| 2005/0119679 A1 | 6/2005 | Rabiner et al. | |
| 2005/0130098 A1 | 6/2005 | Warner | |
| 2005/0187513 A1 | 8/2005 | Rabiner et al. | |
| 2005/0197131 A1 | 9/2005 | Ikegami | |
| 2005/0209560 A1 | 9/2005 | Boukhny et al. | |
| 2005/0236936 A1 | 10/2005 | Shiv et al. | |
| 2005/0245888 A1 | 11/2005 | Cull | |
| 2005/0261628 A1 | 11/2005 | Boukhny et al. | |
| 2005/0267504 A1 | 12/2005 | Boukhny et al. | |
| 2006/0035585 A1 | 2/2006 | Washiro | |
| 2006/0036180 A1 | 2/2006 | Boukhny et al. | |
| 2006/0041220 A1 | 2/2006 | Boukhny et al. | |
| 2006/0046659 A1 | 3/2006 | Haartsen et al. | |
| 2006/0074405 A1 * | 4/2006 | Malackowski et al. | 606/1 |
| 2006/0078448 A1 | 4/2006 | Holden | |
| 2006/0114175 A1 * | 6/2006 | Boukhny | 345/24 |
| 2006/0145540 A1 * | 7/2006 | Mezhinsky | 307/119 |
| 2006/0219049 A1 | 10/2006 | Horvath et al. | |
| 2006/0219962 A1 | 10/2006 | Dancs et al. | |
| 2006/0224107 A1 | 10/2006 | Claus et al. | |
| 2006/0236242 A1 | 10/2006 | Boukhny et al. | |
| 2007/0016174 A1 | 1/2007 | Millman et al. | |
| 2007/0049898 A1 | 3/2007 | Hopkins et al. | |
| 2007/0060926 A1 | 3/2007 | Escaf | |
| 2007/0073214 A1 | 3/2007 | Dacquay et al. | |
| 2007/0073309 A1 | 3/2007 | Kadziauskas et al. | |
| 2007/0078379 A1 | 4/2007 | Boukhny et al. | |
| 2007/0085611 A1 | 4/2007 | Gerry et al. | |
| 2007/0107490 A1 | 5/2007 | Artsyukhovich et al. | |
| 2007/0231205 A1 | 10/2007 | Williams et al. | |
| 2007/0249942 A1 | 10/2007 | Salehi et al. | |
| 2008/0033342 A1 | 2/2008 | Staggs | |
| 2008/0066542 A1 | 3/2008 | Gao | |
| 2008/0067046 A1 | 3/2008 | Dacquay et al. | |
| 2008/0082040 A1 | 4/2008 | Kubler et al. | |
| 2008/0112828 A1 | 5/2008 | Muri et al. | |
| 2008/0114289 A1 | 5/2008 | Muri et al. | |
| 2008/0114290 A1 | 5/2008 | King et al. | |
| 2008/0114291 A1 | 5/2008 | Muri et al. | |
| 2008/0114300 A1 | 5/2008 | Muri et al. | |
| 2008/0114311 A1 | 5/2008 | Muri et al. | |
| 2008/0114312 A1 | 5/2008 | Muri et al. | |
| 2008/0114372 A1 | 5/2008 | Edwards et al. | |
| 2008/0114387 A1 * | 5/2008 | Hertweck | A61F 9/00745 606/170 |
| 2008/0125695 A1 | 5/2008 | Hopkins et al. | |
| 2008/0125697 A1 | 5/2008 | Gao | |
| 2008/0125698 A1 | 5/2008 | Gerg et al. | |
| 2008/0129695 A1 * | 6/2008 | Li | 345/163 |
| 2008/0146989 A1 | 6/2008 | Zacharias | |
| 2008/0243105 A1 | 10/2008 | Horvath | |
| 2008/0262476 A1 | 10/2008 | Krause et al. | |
| 2008/0281253 A1 | 11/2008 | Injev et al. | |
| 2008/0294087 A1 | 11/2008 | Steen et al. | |
| 2008/0312594 A1 | 12/2008 | Urich et al. | |
| 2009/0005712 A1 | 1/2009 | Raney | |
| 2009/0005789 A1 | 1/2009 | Charles | |
| 2009/0048607 A1 | 2/2009 | Rockley | |
| 2009/0124974 A1 | 5/2009 | Crank et al. | |
| 2009/0163853 A1 | 6/2009 | Cull et al. | |
| 2010/0036256 A1 | 2/2010 | Boukhny et al. | |
| 2010/0069825 A1 | 3/2010 | Raney | |
| 2010/0069828 A1 | 3/2010 | Steen et al. | |
| 2010/0152685 A1 | 6/2010 | Goh | |
| 2010/0185150 A1 | 7/2010 | Zacharias | |
| 2010/0249693 A1 | 9/2010 | Links | |
| 2010/0280435 A1 | 11/2010 | Raney et al. | |
| 2011/0092924 A1 | 4/2011 | Wong et al. | |
| 2011/0092962 A1 | 4/2011 | Ma et al. | |
| 2011/0098721 A1 | 4/2011 | Tran et al. | |
| 2011/0160646 A1 | 6/2011 | Kadziauskas et al. | |
| 2012/0065580 A1 | 3/2012 | Gerg et al. | |
| 2012/0083800 A1 | 4/2012 | Andersohn | |
| 2013/0072853 A1 | 3/2013 | Wong et al. | |
| 2013/0245543 A1 | 9/2013 | Gerg et al. | |

(56) References Cited

U.S. PATENT DOCUMENTS

| | | |
|---|---|---|
| 2013/0289475 A1 | 10/2013 | Muri et al. |
| 2013/0303978 A1 | 11/2013 | Ross |

FOREIGN PATENT DOCUMENTS

| | | |
|---|---|---|
| EP | 56019 A1 | 7/1982 |
| EP | 424687 A1 | 5/1991 |
| EP | 619993 A1 | 10/1994 |
| EP | 1010437 A1 | 6/2000 |
| EP | 1072285 A1 | 1/2001 |
| EP | 1113562 A1 | 7/2001 |
| EP | 1310267 A2 | 5/2003 |
| EP | 1464310 A1 | 10/2004 |
| EP | 1469440 A2 | 10/2004 |
| EP | 1550406 A2 | 7/2005 |
| EP | 1704839 | 9/2006 |
| EP | 1779879 A1 | 5/2007 |
| EP | 1787606 A1 | 5/2007 |
| EP | 1849443 A1 | 10/2007 |
| EP | 1849444 A1 | 10/2007 |
| EP | 1857128 A1 | 11/2007 |
| EP | 1867349 A1 | 12/2007 |
| EP | 1310267 B1 | 1/2008 |
| EP | 1873501 A1 | 1/2008 |
| EP | 1900347 A1 | 3/2008 |
| EP | 1925274 A2 | 5/2008 |
| EP | 1867349 B1 | 11/2008 |
| ES | 2264369 A1 | 12/2006 |
| GB | 2230301 A | 10/1990 |
| GB | 2352887 A | 2/2001 |
| GB | 2438679 A | 12/2007 |
| JP | S5724482 A | 2/1982 |
| JP | S58167333 A | 10/1983 |
| JP | 2008188110 A | 8/2008 |
| WO | WO9220310 A1 | 11/1992 |
| WO | 9315777 A2 | 8/1993 |
| WO | WO9317729 A1 | 9/1993 |
| WO | WO9324082 A1 | 12/1993 |
| WO | 9405346 A1 | 3/1994 |
| WO | WO9632144 A1 | 10/1996 |
| WO | 9737700 A1 | 10/1997 |
| WO | WO9818507 A1 | 5/1998 |
| WO | WO9917818 A1 | 4/1999 |
| WO | WO0000096 A1 | 1/2000 |
| WO | WO0070225 A1 | 11/2000 |
| WO | 0122696 A1 | 3/2001 |
| WO | 0226286 A2 | 4/2002 |
| WO | 0228449 A2 | 4/2002 |
| WO | WO0234314 A1 | 5/2002 |
| WO | 03102878 A1 | 12/2003 |
| WO | 04096360 A1 | 11/2004 |
| WO | 2004114180 A1 | 12/2004 |
| WO | WO05084728 A2 | 9/2005 |
| WO | WO05092023 A2 | 10/2005 |
| WO | WO05092047 A2 | 10/2005 |
| WO | WO06101908 A2 | 9/2006 |
| WO | WO06125280 A1 | 11/2006 |
| WO | WO2007121144 A1 | 10/2007 |
| WO | 2007149637 A2 | 12/2007 |
| WO | WO2007143677 A2 | 12/2007 |
| WO | WO2007143797 A1 | 12/2007 |
| WO | WO2008030872 A1 | 3/2008 |
| WO | WO 2008/060859 | 5/2008 |
| WO | WO2008060902 A1 | 5/2008 |
| WO | WO2008060995 A1 | 5/2008 |
| WO | 2009123547 A1 | 10/2009 |
| WO | WO2010054146 A1 | 5/2010 |
| WO | WO2010054225 A2 | 5/2010 |
| WO | 2010151704 A1 | 12/2010 |
| WO | 2012151062 A1 | 11/2012 |
| WO | 2013142009 A1 | 9/2013 |
| WO | 2015009945 A1 | 1/2015 |

OTHER PUBLICATIONS

International Search Report for Application No. PCT/US07/083875, dated May 7, 2008, 4 pages.
International Search Report for Application No. PCT/US07/083880, dated May 30, 2008, 4 pages.
International Search Report for Application No. PCT/US07/084157, dated Apr. 1, 2008, 3 pages.
International Search Report for Application No. PCT/US07/084163, dated Apr. 2008, 3 pages.
International Search Report for Application No. PCT/US08/064240, dated Oct. 29, 2008, 3 pages.
International Search Report for Application No. PCT/US08/071704, dated Nov. 26, 2008, 3 pages.
International Search Report for Application No. PCT/US08/072974, dated Feb. 23, 2009, 2 pages.
International Search Report for Application No. PCT/US2009/052473, dated Nov. 2009, 3 pages.
"Phacoemulsification. Oct. 12, 2006. Wikipedia.com. Jun. 19, 2009 <http://en.wikipedia.org/wiki/Phacoemulsification>,", 2 pages.
Boyd, "Preparing for the Transition" in: The Art and the Science of Cataract Surgery, Chapter 7, 2001, pp. 93-133.
Definition of "Parameter", Retrieved from the Internet: URL: http://dictionary.reference.com/browse/parameter, Retrieved on Aug. 9, 2016.
English Human Translation of JP57024482 from Feb. 9, 1982.

* cited by examiner

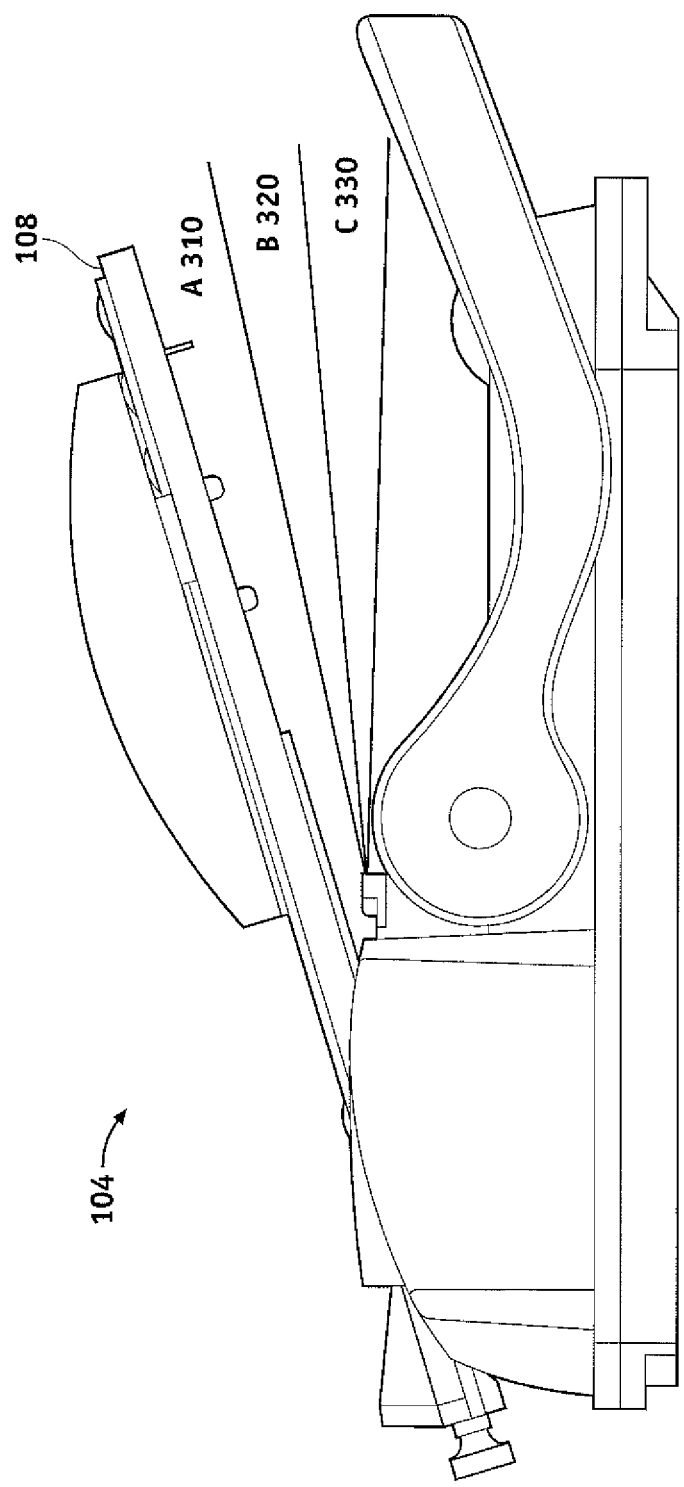

METHOD FOR PROGRAMMING FOOT PEDAL SETTINGS AND CONTROLLING PERFORMANCE THROUGH FOOT PEDAL VARIATION

TECHNICAL FIELD OF THE INVENTION

The present invention relates generally to medical apparatuses; more particularly, to foot-operated controls for surgical apparatuses. Numerous types of apparatuses include as part of the apparatus, a hand-held medical implement or tool. Operation of the tool requires control of various operating settings or functions.

BACKGROUND OF THE INVENTION

Ophthalmic surgical apparatuses such as a phacoemulsification apparatus typically include operating controls for regulating settings or functions of the apparatus. Such phacoemulsification apparatus is particularly directed for surgically removing the natural, crystalline lenses from cataractic eyes prior to the insertion of an artificial intraocular lens.

Such apparatus typically includes a control cabinet, power supply, one or more pumps as well as associated electronic hardware for operating a multifunction handheld surgical implement in order to sonically emulsify eye tissue, irrigate the eye with a saline solution, and aspirate the emulsified lens from the eye.

In view of the handheld instrumentation necessary for a phacoemulsification procedure, foot controls are frequently provided in order to facilitate use of the handpiece by delegating other control functions to the foot pedal device.

Any number of foot pedal device systems have been utilized which included a variety of pneumatic and electrical actuators to control the ophthalmic surgical apparatus.

Improved foot pedal control systems, such as that described in U.S. Pat. No. 4,983,901 provide for a virtually unlimited number of control variations and modes for operating phacoemulsification apparatuses. Additional single linear and dual linear foot pedal patents include U.S. Pat. Nos. 5,268,624; 5,342,293; 6,260,434; 6,360,630; 6,452,120; 6,452,123; and 6,674,030.

However, despite the output from such foot pedals in regulating or controlling the apparatus, the pedal must be user friendly in order to provide a surgeon comfort and reliability in its use so as not to initiate disruption of the surgeon's concentration when performing surgery.

As may be expected, there are many types of foot pedals, but no common way to program the settings that are available for each type. Currently there are static graphical screens that when a user presses a button on the display screen they are presented with menus to select different options to be programmed into the foot pedal; however, until the present invention there was no interface between the footpedal and the display screen to assist in setting the appropriate options for the user.

Thus, it is desirable to have a unified interface for achieving an intuitive way of programming any type of foot pedal attached to a system, wherein the interface is graphical in nature and can receive feedback from the foot pedal and display the information in real time on a display screen. The present invention fulfills that need.

Additionally, there is a need to immediately access multiple pre-programmed memory settings during a surgical procedure. For example, during a phacoemulsification procedure, the surgeon may need or want to switch between multiple pre-programmed memory settings to address issues arising during surgery, such as different lens densities, different situations, and/or different portion of the surgery, e.g. initiation of emulsification vs. cleaning/polishing the capsule. Prior to the present invention, the surgery had to be halted until the surgeon or user could complete the change. Thus, it is desirable to have a mechanism for accessing multiple pre-programmed memory settings and the present invention fulfills that need.

SUMMARY OF THE INVENTION

The present invention pertains to a method for programming one or more foot pedal settings, comprising: (1) selecting a switch or a directional movement of a treadle located on a foot pedal; (2) displaying one or more programming options for the selected switch or directional movement of the treadle on a display; (3) toggling through the one or more programming options, wherein the toggling is performed by moving the treadle; and (4) selecting one of the programming options available for the selected switch or directional movement of the treadle. The selecting may be performed by one selected from the group consisting of clicking an icon on the display, pressing a switch on the foot pedal, moving the treadle, voicing a command, and combinations thereof. The one or more programming options is selected from the group consisting of irrigation, aspiration, ultrasonic power, vitrectomy, bottle height, pump speed, pump type, flow rate, and vacuum level. The present invention also pertains to selecting a second switch or second directional movement of the treadle and deactivating or locking the second switch or second directional movement.

The present invention also pertains to a method for programming surgical settings for a foot pedal, comprising: (1) selecting a directional movement of a treadle located on the foot pedal, wherein the directional movement of the treadle is selected from the group consisting of pitch and yaw and wherein the selecting of the directional movement is performed by moving the treadle; (2) displaying one or more surgical settings for the selected directional movement on a display; and (3) selecting one or more surgical settings, wherein the selecting of the one or more surgical settings is performed by one selected from the group consisting of the foot pedal, the display, a voice command, and combinations thereof. The present invention further comprises moving the foot pedal in the selected directional movement by depressing the treadle or yawing the treadle; placing the treadle in a first starting location for a first selected surgical setting; confirming the first starting location; placing the treadle in a first ending location for the first selected surgical setting; and confirming the first ending location, wherein the confirming is performed by one selected from the group consisting of clicking an icon on the display, pressing a switch on the foot pedal, moving the treadle, voicing a command and combinations thereof. Additional starting and ending locations for other settings may also be selected and programmed.

The present invention also pertains to a method of using a foot pedal to select multiple pre-programmed settings, comprising selecting a direction of movement of a treadle of the foot pedal, wherein the direction is selected from the group consisting of pitch and yaw; and moving the treadle in the selected direction to one or more selected from the group consisting of: a first location, wherein the first location is a first pre-programmed setting; a second location, wherein the second location is a second pre-programmed setting; and a third location, wherein the third location is a third pre-programmed setting.

The present invention also pertains to a method for selecting pre-programmed memory settings for a surgical procedure using a foot pedal, comprising moving a treadle of the foot pedal to a first location within a directional axis selected from the group consisting of pitch and yaw, wherein the first location activates a first pre-programmed memory setting; and moving the treadle within a plane of the first location to activate one or more control settings of the first pre-programmed memory setting. The method further comprises moving the treadle of the foot pedal to a second location within the directional axis, wherein the second location activates a second pre-programmed memory setting; and moving the treadle within a plane of the second location to activate one or more control settings of the second pre-programmed memory setting. Additionally, the method further comprising moving the treadle of the foot pedal to a third location within the directional axis, wherein the third location activates a third pre-programmed memory setting; and moving the treadle within a plane of the third location to activate one or more control settings of the third pre-programmed memory setting.

The present invention also pertains to a foot pedal, comprising a treadle, wherein the treadle is capable of moving in at least one direction selected from the group consisting of pitch and yaw, and wherein at least one of the directional movements of the treadle is capable of acting as a switch. Additionally, the present invention pertains to a method of programming a linear foot pedal, comprising selecting a directional movement of a treadle of the linear foot pedal, wherein the directional movement is selected from the group consisting of pitch and yaw; and programming the selected directional movement to function as a switch.

BRIEF DESCRIPTION OF THE DRAWINGS

The present invention is best understood with reference to the following detailed description of the invention and the drawings in which:

FIG. 6 is a profile view of a foot pedal showing an embodiment having pre-programmed memory settings (zones) in a pitch direction.

DETAILED DESCRIPTION OF THE INVENTION

Reference will now be made in detail to embodiments of the invention, examples of which are illustrated in the accompanying drawings. While the invention will be described in conjunction with the embodiments, it will be understood that they are not intended to limit the invention to those embodiments. On the contrary, the invention is intended to cover alternatives, modifications, and equivalents, which may be included within the spirit and scope of the invention as defined by the appended claims.

The present invention may be used with any foot pedal known in the art for use with medical apparatuses, including dual linear foot pedals and single linear foot pedals.

Figure 1:
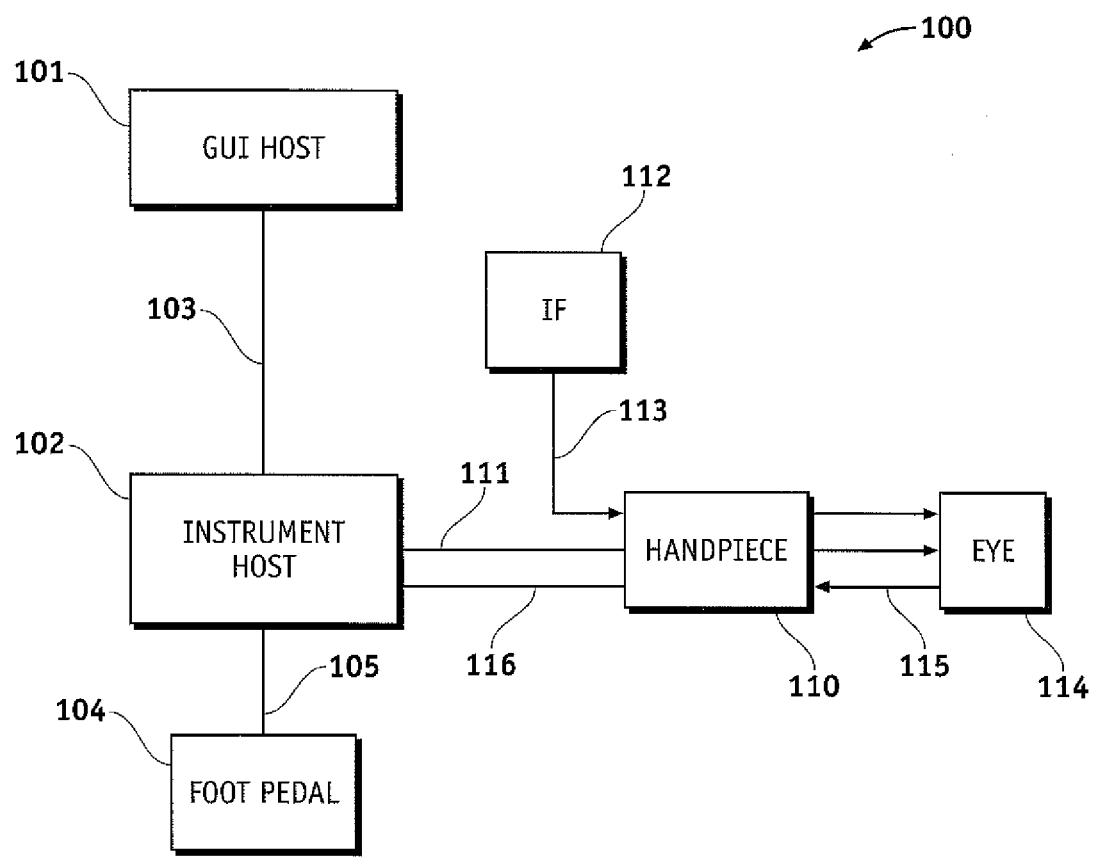
FIG. 1 illustrates an exemplary phacoemulsification/vitrectomy system in a functional block diagram.

FIG. 1 illustrates an exemplary phacoemulsification/vitrectomy system 100 in a functional block diagram to show the components and interfaces for a safety critical medical instrument system that may be employed in accordance with an aspect of the present invention. A serial communication cable 103 connects GUI host 101 and instrument host 102 module for the purposes of controlling the surgical instrument host 102 by the GUI host 101. GUI host 101 and instrument host 102, as well as any other component of system 100, may be connected wirelessly. Instrument host 102 may be considered a computational device in the arrangement shown, but other arrangements are possible. Foot pedal 104 and instrument host 102 may provide control and feedback by exchanging data between foot pedal 104 and the instrument host 102, between software subsystems within instrument host 102, between instrument host 102 and subsystems external to the instrument host 102 and/or GUI host 101, or between subsystems external to instrument host 102 and/or GUI host 101. Instrument host 102 may include various programs and functionality, including but not limited to applications functioning to conduct an ophthalmic surgical procedure.

A switch module associated with foot pedal 104 may transmit control signals relating internal physical and virtual switch position information as input to the instrument host 102 over serial communications cable 105 (although foot pedal 104 may be connected wirelessly). Instrument host 102 may provide a database file system for storing configuration parameter values, programs, and other data saved in a storage device (not shown). In addition, the database file system may be realized on the GUI host 101 or any other subsystem (not shown) that could accommodate such a file system.

The phacoemulsification/vitrectomy system 100 has a handpiece 110 that includes a needle and electrical means, typically a piezoelectric crystal, for ultrasonically vibrating the needle. The instrument host 102 supplies power on line 111 to a phacoemulsification/vitrectomy handpiece 110. An irrigation fluid source 112 can be fluidly coupled to handpiece 110 through line 113. The irrigation fluid and ultrasonic power are applied by handpiece 110 to an eye, or affected area or region, indicated diagrammatically by block 114. Alternatively, the irrigation source may be routed to eye 114 through a separate pathway independent of the handpiece. Aspiration is provided to eye 114 by a pump(s) (not shown), such as a peristaltic pump and/or a vacuum pump, via the instrument host 102, through lines 115 and 116.

Figure 2:
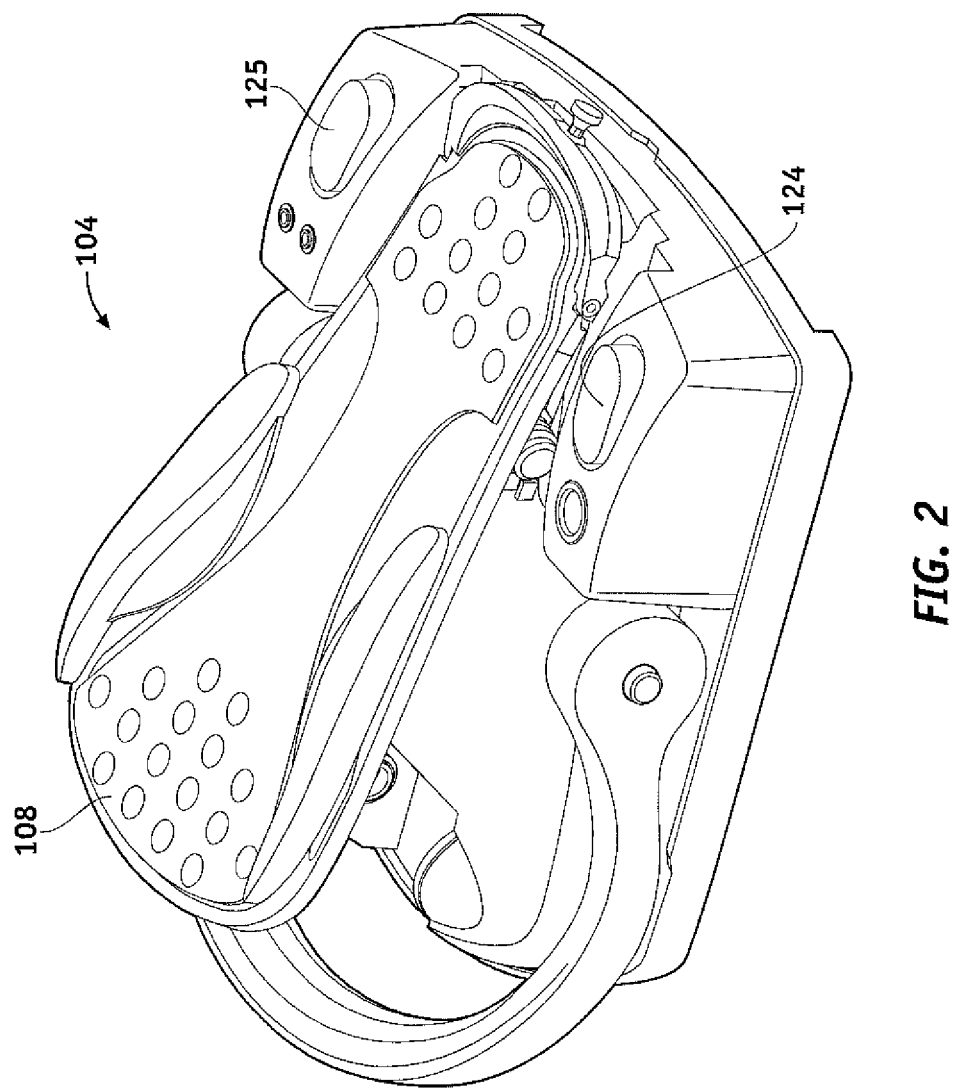
FIG. 2 is a schematic of a foot pedal showing features of the foot pedal.

As shown in FIG. 2, foot pedal 104 may comprise a treadle 108 and one or more switches (e.g. left switch 124 and right switch 125). Treadle 108 may move in a pitch direction and in a yaw direction. The directional movement of treadle 108 may control various programming/surgical settings selected by a user.

According to an embodiment, the present invention pertains to programming a foot pedal and switches located therewith that is used with a medical device and/or medical device system. A user may select any switch or directional movement (pitch (up and down in a vertical plane) or yaw (rotation of a treadle from left to right and vice versa (side to side) in a horizontal plane)) available on the foot pedal for programming by activating the switch and/or moving a treadle located on the foot pedal or by selecting a foot pedal feature on a display screen. The user may also select a foot pedal feature by voice commands. The user's selection tells an instrument host or controller which switch or directional movement has been selected and the programming options available for the selected switch or directional movement are displayed on the display screen. Using the foot pedal, the display screen, and/or voice command, the user can navigate through different options/settings to select one or more options, such as by toggling through a list of options, preferably using the foot pedal and/or the display screen. The user may confirm the chosen option(s)/setting(s) for the particular switch or directional movement by engaging the foot pedal, clicking on the display screen, using a voice command or any combination thereof to write into the memory of the medical device system the option(s)/setting(s). The speed of the yaw or pitch movement (e.g. a quick tap of the treadle) may also be used to set or confirm a programming setting, feature selection, and/or any other selection. The control and feel of the depression and/or movement of the treadle and/or switch provides the user with the ability to program custom settings that suit the user's foot position(s), comfort, and/or particular style of surgery. The user may also set the sensitivity and/or how the movement of the treadle responds with respect to the programming settings and/or parameters thereof, e.g. the proportional response between the movement of the treadle and the level of ultrasonic power.

With linear foot pedals known in the art, the user can set the three available positions of the treadle movement using the display screen, but not until the present invention could the settings be made using both the foot pedal and the display screen. The term "display" or "display screen" as used herein shall mean a graphical user interface (GUI), a screen, a monitor, touch screen, or any other device known in the art for displaying a visual picture or representation. The three traditional positions ("position" as used herein shall mean a range of travel (movement) for a particular setting, e.g. irrigation) of the treadle in phacoemulsification include position 1 for irrigation; position 2 for irrigation and aspiration; and position 3 for irrigation, aspiration, and ultrasonic power.

When the foot pedal is in a resting position, there are no pumps running or ultrasonic power being exerted. Position 1 allows for irrigation of fluid to the eye from an irrigation source. The travel of the treadle within the first position may control the flow rate of fluid into the eye. Position 2 activates one or more pumps that are capable of increasing flow of fluid into and through the eye, aspirate fluid and lens material from the eye, and/or venting towards the eye to relieve pressure build up in the medical device system. The travel within position 2 may be programmed to control how the one or more pumps operate. For example, as the user continues to travel farther within a position, the aspiration rate may increase, the pump rate may increase, or the vacuum pressure may increase. Position 3 activates the ultrasound energy, which is used to help emulsify and/or break up the lens material. The travel within position 3 may be programmed to control, inter alia, how much power is exerted on the lens material, how the power is exerted (e.g. burst, pulse, etc.), and the length of time the power is on (duty cycle). With the present invention the user may move the treadle to various locations within the available degree of movement to set where each option begins and ends, as well as the type of control occurring within each beginning and ending, e.g., percent power distribution, type of pulses, vacuum level distribution, etc. The user may also set within a selected range of movement of the treadle how the particular programming setting will perform. For example, the ultrasonic power may increase linearly as the foot pedal is depressed or the power may increase at a set increment until a particular degree of travel of the treadle has been reached and then increments may become smaller or larger depending upon the user's preference. See FIGS. 3A and 3B which shows graphical examples of how a parameter/programming setting may react as the foot pedal is moved in a yaw or pitch direction.

For a dual linear foot pedal, the user may program the pitch directional movement and/or the yaw directional movement to correspond to one or more settings. To program a directional movement, the user selects either the pitch or the yaw directional movement of the treadle of the foot pedal by indicating the selection on a display screen, by moving the treadle in the selected directional movement, by activating a switch on the foot pedal itself, by voice command, or combinations thereof. Once the user has made a selection, the display screen will show all of the available programming settings for the selected directional movement. The available programming settings include, but are not limited to, irrigation and rate thereof, aspiration and rate thereof, choice of pump and control thereof, vacuum and control thereof, ultrasonic power and control thereof, and combinations thereof. Additional programming settings include use of a combination of pumps or switching between pumps; controlling the linear relationship between movement (travel of the treadle) and the programming setting; proportional relationship between movement and control of a programming setting (e.g. 5 mm (or 2°)=100 mmHg vs. 10 mm (or 4°)=100 mmHg or 5 mm (or 2°)=10 Hz vs. 10 mm (or 4°)=100 Hz); and/or panel movement (constant rate within a particular zone or degree of movement of the treadle) of the programming settings. By depressing the foot pedal or yawing the foot pedal to the left and/or right, the user can coordinate the feel of the foot pedal and its degree of depression or yaw to a particular program setting. Once a first designated location is reached, the user may indicate (confirm) the choice on the display screen or write in (save setting(s) in memory) the particular setting by any other mechanism described herein or known in the art, such as voice command and/or tap switch, and continue moving the foot pedal to a second designated location. Once the second designated location is reached, the user may indicate the choice. The user may continue until all of the desired and/or allowed settings for the directional movement of the foot pedal are set. If the user should exceed a set maximum amount of travel of the foot pedal for a particular setting, the instrument host or controller will indicate such maximum has been met and will prevent the user from setting a designated location outside the permitted range. When the dual linear foot pedal is used as described herein, it allows a user to control the functions, modes, and/or settings, simultaneously by using pitch, yaw, and combinations thereof.

According to an embodiment, upon attachment of a foot pedal to a medical device system, the interface of the system will recognize the type of foot pedal and the features of the foot pedal. A foot pedal may be attached to the medical device system by any mechanism known in the art, including, but not limited to, a wire connection and a wireless connection, e.g. Bluetooth® or IR. A display screen of the medical device system may present the user with a picture or representation of the foot pedal detected. The picture or representation may show all the switches and directional movements available for programming the attached foot pedal.

To program the setting(s) for a right heel switch, the user may push the right heel switch, select the right heel switch on the display screen, or use a voice command. Activating the right heel switch results in the available programming settings for the right heel switch to be displayed on the display screen. The user may select the desired programming settings from the available options by clicking on the screen or may scroll through the available options by moving the treadle of the foot pedal and selecting the setting by clicking on the screen to write that setting to the right heel switch, or use a voice command. Once the desired setting is selected any additional options available to the user for the right heel switch will be shown on the display screen. Again, following the technique used to make the first selection for the right heel switch, the user may continue programming his desired settings for that switch or any other feature of the foot pedal.

Figure 3A:
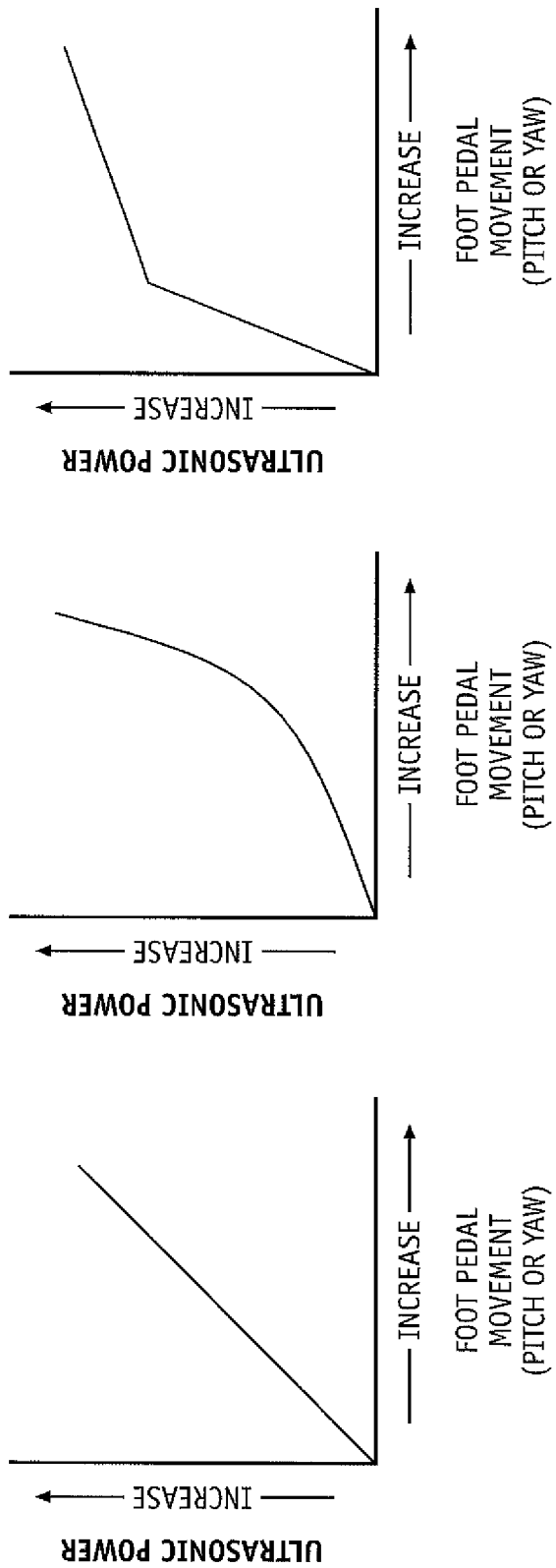
FIG. 3A illustrates graphical examples of foot pedal movement and ultrasonic power levels.
Figure 3B:
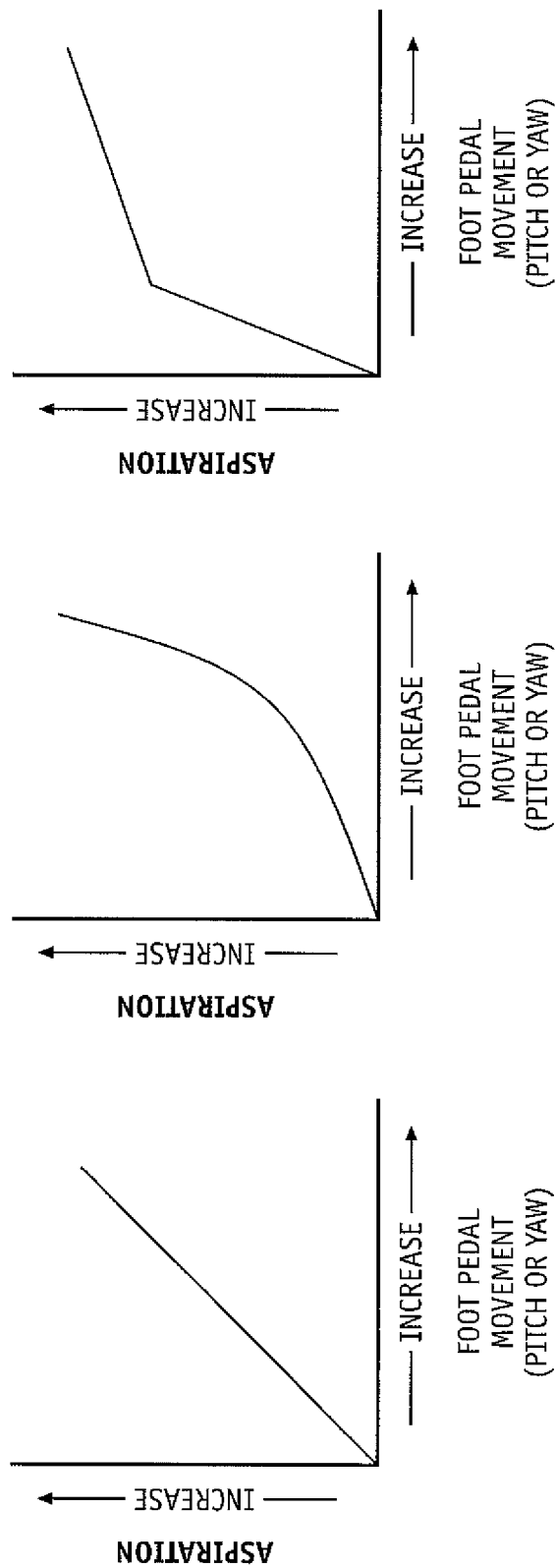
FIG. 3B illustrates graphical examples of foot pedal movement and aspiration levels.

Any options available for a particular medical device system may be employed with the present invention. For example, with a phacoemulsification system the available settings may include, but are not limited to, irrigation, aspiration, vacuum level, flow rate, pump type (flow based and/or vacuum based), pump speed, ultrasonic power (type and duration, e.g. burst, pulse, duty cycle, etc.) bottle height adjustment, linear control of settings, proportional control of settings, panel control of settings, and type (or "shape") of response as illustrated in FIGS. 3A and 3B. The user may program the starting point and ending point in the pitch direction for a first program setting, such as irrigation, by depressing the treadle to the desired starting point and clicking on the screen to write in that setting. The user may also desire the first starting point be the resting state of the treadle, i.e. before any movement of the treadle. The user continues depressing the treadle from the first starting point to a first ending point and again writes in the setting. The user may continue programming additional starting and ending points in the pitch direction for other desired settings using the treadle.

The interface provides feedback to the user should the selected starting and ending points fall outside preset thresholds to ensure all the desired settings for the pitch direction of the treadle will fit within the degree of movement permitted by the foot pedal.

Other mechanisms for setting and/or programming a particular setting may be employed with the present invention, including, but not limited to, clicking on an icon on a display screen using a mouse or touch screen, depressing a button/switch on a foot pedal, voice activated commands and/or combinations thereof.

Figure 3C:
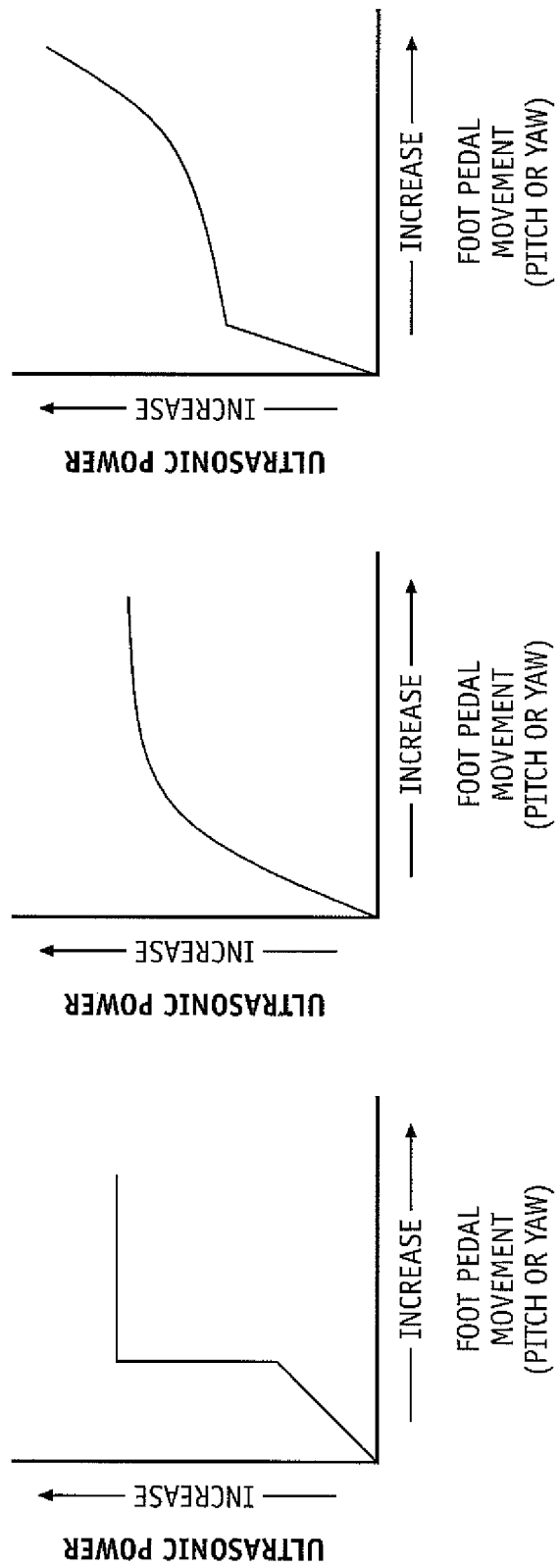
FIG. 3C illustrates graphical examples of foot pedal movement and ultrasonic power levels.
Figure 3D:
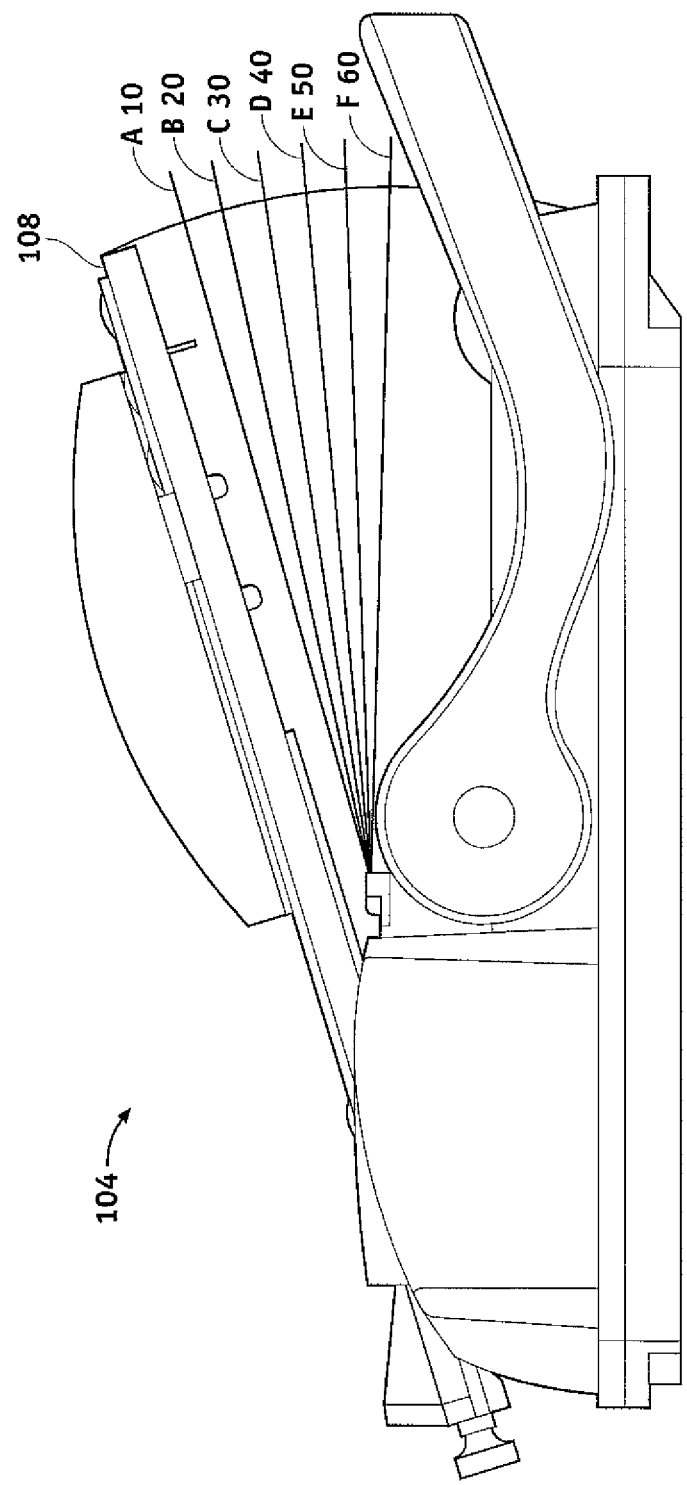
FIG. 3D is a profile view of a foot pedal showing the movement of a treadle in a pitch direction.

FIG. 2 is a schematic of foot pedal 104 that may be used with the present invention. Foot pedal 104 comprises treadle 108, left switch 124, and right switch 125. FIG. 3D is a profile view of foot pedal 104. In FIG. 3D, location A 10 may indicate a starting point in the pitch direction of treadle 108 for a first setting. Location B 20 may indicate the ending point in the pitch direction for the first setting. Location C 30 may indicate the starting point in the pitch direction for a second setting and location D 40 may indicate the ending point of the second setting. Location E 50 may indicate the starting point in the pitch direction for a third setting and location F 60 may indicate the ending point of the third setting. Location B 20 and location C 30 may be located at substantially the same point, but the interface can prevent location C 30 from occurring before location B 20. The interface may also prevent a large degree of movement from location A 10 to location B 20 for the first setting and a large degree of movement from location C 30 to location D 40 to prevent inadequate or no degree of movement for the third setting (location E 50 to location F 60). Also, in FIG. 3D location B 20 to location C 30 or any other locations within the degree of movement of the treadle may be a dead zone or gap where no programming settings occur. This may be programmed by the user as a safety feature and/or based on personal preferences.

If a degree of movement from a starting location to an ending location exceeds a preset threshold, the user will be notified by, but not limited to, a visual indication on the display screen and/or an audible sound/voice emitted from the medical device system.

Figure 4:
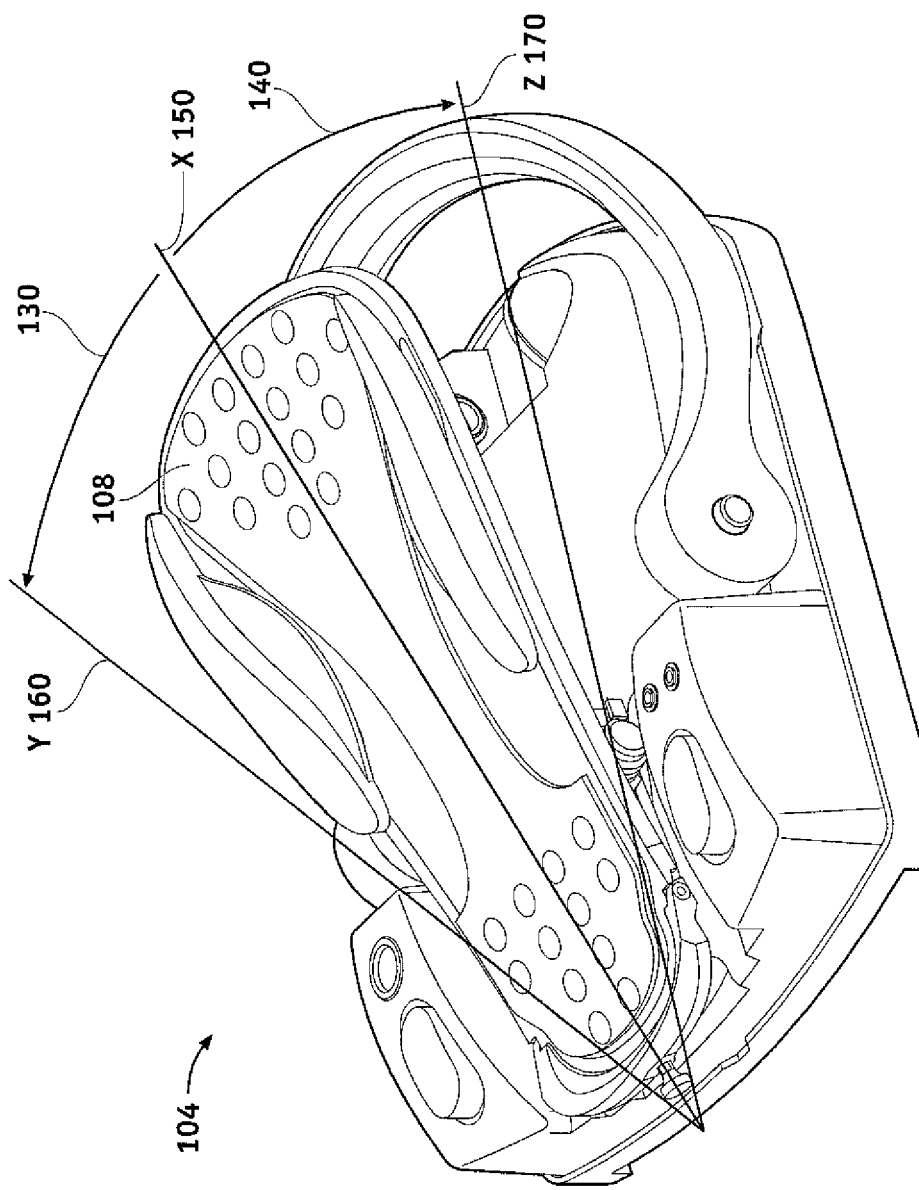
FIG. 4 is a schematic of a foot pedal showing the movement of a treadle in a yaw direction.

FIG. 4 illustrates another example of an embodiment of the present invention. The yaw directional movement of treadle 108 of foot pedal 104 may be programmed to a user's preferences based upon the available programming settings for the yaw directional movement. The user may begin programming the yaw directional movement of treadle 108 by clicking on the feature displayed on the display screen, by moving treadle 108 to the left, arrow 130, and/or to the right, arrow 140, and/or using a voice command. The available programming settings will be displayed to the user on the display screen. The user may program the yaw directional movement of treadle 108 to be a switch, such that movement from location X 150 (the resting location shown in FIG. 4) to any of the following locations results in an on/off setting: location Y 160, to location Z 170, to any location between location X 150 and location Y 160, or to any place between location X 150 and location Z 170. For example, moving treadle 108 from location X 150 to location Y 160 causes a balanced saline solution (BSS) bottle to move in an upward direction (not shown) and may be stopped by moving treadle 108 from location Y 160 back to location X 150. The BSS bottle may be moved in a downward direction by moving treadle 108 from location X 150 to location Z 170.

Additional option settings may be employed and are envisioned by the present invention. For example, moving treadle 108 toward or to location Y 160 from location X 150 may start the movement of the BSS bottle in a selected direction and movement from location X 150 back towards or to location Y 160 stops the movement of the BSS bottle. The degree of movement in the yaw and/or pitch direction to activate a switch function may be set to the user's preference, e.g. 15° movement from the starting location.

The yaw directional movement of treadle 108 may be programmed as a linear control, such that movement from location X 150 toward location Y 160 activates a selected setting, which adjusts as treadle 108 moves closer to location Y 160. For example, yaw directional movement 130 may be programmed to control aspiration. The user may program yaw directional movement 130 such that the closer treadle 108 moves towards location Y 160 and away from location X 150, the more the pump turns and/or vacuum increases causing the rate of aspiration to increase. For example, see FIG. 3B.

The left directional yaw movement may also be programmed to act as a switch, while the right directional yaw movement may have a linear function, and vice versa. For example, movement of treadle 108 to the left may turn on the aspiration and movement of treadle 108 to the right may control the level of aspiration such that as treadle 108 moves farther to the right the aspiration rate increases. In another embodiment, the left (or right yaw) may be a switch that changes the surgical mode on the fly to allow the user more control over the procedure. Any programmable features may be incorporated with the present invention in any directional movement, location within the directional movement, switch, or combination thereof.

Using the foot pedal as described herein, the user may also set the amount of vacuum, ultrasonic power, etc. at different degrees of movement for pitch and/or yaw and whether there is a dead zone between starting and ending locations for a particular setting and/or pre-programmed memory setting. For example, a user may set 0° to 10° directional movement for a first setting and 11° to 13° directional movement as a dead zone, wherein a second setting may begin at 14° directional movement (0° represents the treadle in its resting (neutral) location). It is also envisioned that one direction of the yaw (left or right) may be a linear control and a switch depending upon how far the treadle travels in the particular yaw direction. For example, the user may have linear control over ultrasonic power up to 50% of the available travel of the treadle in one direction and passing the 50% threshold in the same direction results in a switch that turns the power up to a maximum power level set by the user (e.g. see FIG. 3C) or results in a faster increase in power as the treadle is moved (e.g. see FIG. 3A). It is also envisioned that the yaw movement can be an extension of the linear control of the pitch and vice versa, or to provide a power or vacuum boost.

The foot pedal may also be programmed such that yawing to the left turns on a peristaltic pump and yawing to the right turns on a venturi pump, and vice versa. Further, movement in the pitch direction in either yaw direction may control the flow level of the pump and/or vacuum level of the pump. The foot pedal may also be programmed such that the movement of the treadle in the left yaw direction controls longitudinal movement of a phaco needle and the movement of the treadle in the right yaw direction controls traverse movement of a phaco needle, and vice versa. The pitch directional movement may also be programmed for these settings.

According to an embodiment, multiple pre-programmed memory settings may be accessed using the foot pedal. For example, a pre-programmed memory setting may comprise one or more modes that a user may switch to or cycle through, e.g. each mode may have a particular maximum vacuum and/or maximum ultrasonic power, which the user can change by changing modes. A user may pre-program multiple surgery settings based upon different surgical techniques or situations encountered during surgery, such as, but not limited to, the density of the lens, intraoperative exigencies, and different parts of the procedure, such as sectioning, chopping, and/or polishing. Typically, for a user to switch between pre-programmed memory settings, the user must stop the surgical procedure and change to the desired pre-programmed memory setting or change the type of pump the user would like to use (e.g. venturi to peristaltic). However, with the present invention the user may change from a first pre-programmed memory setting to a second pre-programmed memory setting by activating the foot pedal.

Figure 5:
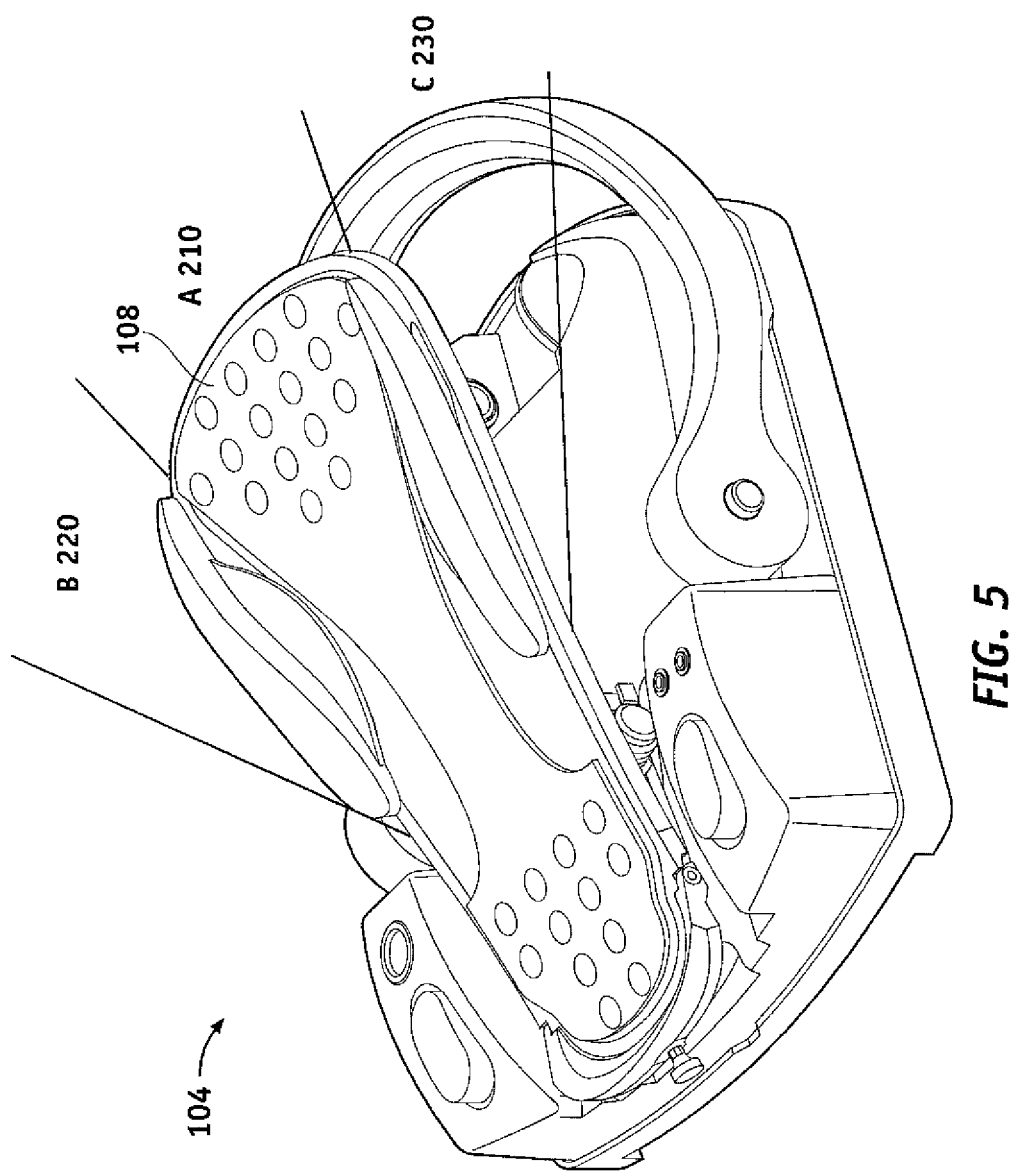
FIG. 5 is a schematic of a foot pedal showing an embodiment having pre-programmed memory settings (zones) in a yaw direction.

For example, referring to FIG. 5, foot pedal 104 has been divided into three distinct yaw zones, zone A 210, zone B 220, and zone C 230 (the zones may be of any size and may be set by the user). Zone A 210 (the resting location for treadle 108) controls one of three pre-programmed memory settings. A first pre-programmed memory setting may be used when treadle 108 is within zone A 210. Moving treadle 108 in a pitch direction of zone A 210, provides control over the programmed settings that make up the pre-programmed memory setting for zone A 210. Moving treadle 108 from zone A 210 to zone B 220 activates a second pre-programmed memory setting and moving treadle 108 in a pitch direction within zone B 210 controls the programmed settings that make up the second pre-programmed memory setting. Finally, a third pre-programmed memory setting may be used when treadle 108 is within zone C 230. Moving treadle 108 to zone C 230 activates a third pre-programmed memory setting and moving treadle 108 in a pitch direction within zone C 230 controls the programmed settings that make up the third pre-programmed setting. All of the pre-programmed memory settings and program settings within the pre-programmed memory settings may be set by the methods disclosed herein. Multiple pre-programmed memory settings may be set in the pitch direction as depicted in FIG. 6 (A 310, B 320, and C 330) and moving treadle 108 in a yaw direction controls the programmed settings for the each of the pre-programmed memory settings. Any number of pre-programmed memory settings may be employed and are envisioned with the present invention.

Other embodiments are envisioned with the present invention and include, but are not limited to: the yaw directional movement as a switch and the pitch directional movement a linear control or vice versa; partial switch and partial linear control for the yaw directional movement and/or pitch directional movement; linear control for both yaw and pitch; fixed panel control in the pitch and/or yaw directional movement or portion thereof; one or more switches programmed for particular features, e.g. a first pump, a second pump, irrigation, coupled with linear control using the yaw and/or pitch to adjust the control of the particular feature programmed and selected; and combinations thereof.

Another embodiment envisioned with the present invention is incorporating a locking feature on the treadle. The locking feature may be a latch or any other locking mechanism or device known in the art for preventing movement of the treadle in the pitch or yaw direction. The locking feature would allow for a user to select one directional movement for activation of various surgery settings and/or parameters as discussed above and deactivate the other directional movement. By locking or deactivating a directional movement of the treadle, the treadle will not move in the deactivated direction and/or no settings and/or parameters will be programmed for the deactivated directional movement. For example, if a user prefers to control various surgery settings and/or parameters using the pitch directional movement only, he may lock and/or deactivate the yaw directional movement.

All references cited herein are hereby incorporated by reference in their entirety including any references cited therein.

Although the present invention has been described in terms of specific embodiments, changes and modifications can be carried out without departing from the scope of the invention which is intended to be limited only by the scope of the claims.

The invention claimed is:
1. A method for programming and operating according to one or more foot pedal settings, comprising:
displaying a plurality of pre-programmed setting selections for a directional movement of a treadle of the foot pedal on a display, wherein the plurality of pre-programmed setting selections is selected from the group consisting of irrigation, aspiration, ultrasonic power, vitrectomy, bottle height, pump speed, pump type, flow rate, and vacuum level;

toggling through pre-programmed setting selections displayed on the display using the foot pedal in order to select from one of the plurality of pre-programmed setting selections;

selecting one of the pre-programmed setting selections displayed on the display to represent the directional movement of the treadle;

positioning the treadle in a starting location for a selected surgical setting and confirming the starting location and positioning the treadle in an ending location for the selected surgical setting and confirming the ending location, wherein confirming comprises performing one selected from the group consisting of clicking an icon on the display, pressing a switch on the foot pedal, moving the treadle, voicing a command, and combinations thereof;

repeating said toggling, selecting, and positioning to establish any additional surgical settings corresponding to directional movements of the treadle; and subsequently operating the foot pedal in accordance with the one or more foot pedal settings within a portion of a surgical procedure.

2. The method of claim 1, wherein the selecting is performed by one selected from the group consisting of clicking an icon on the display, pressing a switch on the foot pedal, moving the treadle, voicing a command, and combinations thereof.

3. The method of claim 1, wherein the foot pedal is used in a phacoemulsification system.

4. The method of claim 1, further comprising setting a type of control for the selected pre-programmed setting selections, wherein the type of control comprises one or more selected from the group consisting of linear control, panel control, proportional control, and switch control with respect to the directional movement of the treadle.

5. The method of claim 4, wherein the setting is performed by one selected from the group consisting of clicking an icon on the display, pressing a switch on the foot pedal, moving the treadle, voicing a command, and combinations thereof.

6. The method of claim 1, further comprising selecting a second switch or a second directional movement of the treadle and deactivating or locking the second switch or the second directional movement of the treadle.

7. A method for programming and operating a foot pedal according to surgical settings, comprising:

displaying a plurality of pre-programmed surgical setting selections for a selected directional movement on a display, wherein the plurality of pre-programmed surgical setting selections is selected from the group consisting of irrigation, aspiration, ultrasonic power, vitrectomy, bottle height, pump speed, pump type, flow rate, and vacuum level;

selecting a surgical setting;

positioning the treadle in a starting location for the surgical setting and confirming the starting location and positioning the treadle in an ending location for the surgical setting and confirming the ending location; and subsequently operating the foot pedal in accordance with the surgical setting within a portion of a surgical procedure;

wherein positioning the treadle and selecting the surgical setting comprises toggling through pre-programmed surgical setting selections displayed on the display using the foot pedal and selecting the surgical setting from the pre-programmed surgical setting selections displayed on the display wherein the confirming is performed by one selected from the group consisting of clicking an icon on the display, pressing a switch on the foot pedal, moving the treadle, voicing a command, and combinations thereof.

8. The method of claim 7, further comprising:

placing the treadle in a second starting location for a second selected surgical setting;

confirming the second starting location;

placing the treadle in a second ending location for the second selected surgical setting; and confirming the second ending location.

9. The method of claim 8, further comprising:

placing the treadle in a third starting location for a third selected surgical setting;

confirming the third starting location;

placing the treadle in a third ending location for the third selected surgical setting; and confirming the third ending location.

10. The method of claim 7, wherein the selecting of one or more surgical settings is performed using the foot pedal.

11. The method of claim 7, wherein the confirming is performed using the display.

12. The method of claim 7, wherein the surgical settings are for an ophthalmic surgical procedure.

13. The method of claim 12, wherein the ophthalmic surgical procedure is phacoemulsification.

14. The method of claim 7, further comprising setting a type of control associated with the surgical setting, wherein the type of control comprises one selected from the group consisting of linear control, panel control, proportional control, and switch control with respect to the directional movement of the treadle.

15. The method of claim 14, wherein the setting is performed by one selected from the group consisting of clicking an icon on the display, pressing a switch on the foot pedal, moving the treadle, voicing a command, and combinations thereof.

16. The method of claim 7, further comprising deactivating or locking a non-selected directional movement of the treadle.

17. A method of using a foot pedal to select from among multiple pre-programmed settings and operate according to selected settings, comprising:

selecting an operational setting by moving the treadle in a selected direction to one or more selected from the group consisting of:

a first location, wherein the first location is a first pre-programmed setting; and a second location, wherein the second location is a second pre-programmed setting;

positioning the treadle at the first location for the first pre-programmed setting and confirming the first location as the starting location of the first pre-programmed setting and positioning the treadle at the second location for the second pre-programmed setting and confirming the second location as the starting location of the second pre-programmed setting, wherein confirming is performed by one selected from the group consisting of clicking an icon on the display, pressing a switch on the foot pedal, moving the treadle, voicing a command, and combinations thereof, and subsequently operating the foot pedal in accordance with the operational settings within a portion of a surgical procedure;

wherein the first pre-programmed setting and the second pre-programmed setting are established by a user toggling through pre-programmed surgical settings displayed to the user on a display using the foot pedal and selecting displayed pre-programmed surgical settings applicable to the first location and second location, respectively, to initially establish a first mode and a second mode.

18. The method of claim 17, wherein the pre-programmed settings comprise one or more modes selected by the user, and wherein the modes are selected from the group consisting of irrigation, aspiration, ultrasonic power, vitrectomy, bottle height, pump speed, pump type, flow rate, and vacuum level.

19. The method of claim 18, further comprising setting a type of control for the one or more modes, wherein the type of control comprises one or more selected from the group consisting of linear control, panel control, proportional control, and switch control with respect to the directional movement of the treadle.

20. The method of claim 19, wherein the setting is performed by one selected from the group consisting of clicking an icon on a display, pressing a switch on the foot pedal, moving the treadle, voicing a command, and combinations thereof.

21. The method of claim 17, wherein the foot pedal is used in a phacoemulsification system.

22. A method for selecting pre-programmed memory settings for and operating in a surgical procedure using a foot pedal, comprising:
  moving a treadle of the foot pedal to a first location within a directional axis, wherein the first location selects a first pre-programmed memory setting to be used in a portion of the surgical procedure;
  moving the treadle to a first perpendicular axis location within a plane perpendicular to the directional axis of the first location to establish one or more control settings of the first pre-programmed memory setting;
  wherein moving the treadle comprises positioning the treadle at a first position for one control setting and confirming the first position as the starting position for the first pre-programmed setting and positioning the treadle at a second position for another control setting and confirming the second position as the starting position of the another control setting, wherein confirming is performed by one selected from the group consisting of clicking an icon on the display, pressing a switch on the foot pedal, moving the treadle, voicing a command, and combinations thereof; and
  subsequently operating the foot pedal in accordance with the pre-programmed memory settings within the portion of the surgical procedure;
  wherein the first pre-programmed memory setting is established by a user toggling through multiple pre-programmed surgical settings displayed to the user on a display using the foot pedal.

23. The method of claim 22, further comprising:
  moving the treadle of the foot pedal to a second location within the directional axis, wherein the second location selects a second pre-programmed memory setting; and
  moving the treadle within a plane perpendicular to the directional axis of the second location to establish one or more control settings of the second pre-programmed memory setting.

24. The method of claim 23, further comprising:
  moving the treadle of the foot pedal to a third location within the directional axis, wherein the third location selects a third pre-programmed memory setting; and
  moving the treadle within a plane perpendicular to the directional axis of the third location to establish one or more control settings of the third pre-programmed memory setting.

25. The method of claim 22, wherein the surgical procedure is an ophthalmic surgical procedure.

26. The method of claim 25, wherein the ophthalmic surgical procedure is phacoemulsification.

27. The method of claim 22, wherein the one or more control settings is selected from the group consisting of irrigation, aspiration, ultrasonic power, vitrectomy, bottle height, pump speed, pump type, flow rate, and vacuum level.

28. The method of claim 27, further comprising setting a type of control for the selected one or more control settings, wherein the type of control comprises one or more selected from the group consisting of linear control, panel control, proportional control, and switch control with respect to the directional movement of the treadle.

29. The method of claim 28, wherein the setting is performed by one selected from the group consisting of clicking an icon on a display, pressing a switch on the foot pedal, moving the treadle, voicing a command, and combinations thereof.

30. A foot pedal comprising:
  a treadle, wherein the treadle is capable of moving in a first direction selected from the group consisting of pitch and yaw;
  wherein movement of the treadle in a plane perpendicular to the first direction establishes a mode by a user toggling through a plurality of available modes displayed to the user on a display using the foot pedal, the user selecting one displayed available mode and positioning the treadle in a first position for one control setting and confirming the first position as the starting position for the one control setting and positioning the treadle at a second position for a second control setting and confirming the second position as the starting position of the second control setting wherein confirming is performed by one selected from the group consisting of clicking an icon on the display, pressing a switch on the foot pedal, moving the treadle, voicing a command, and combinations thereof, and an operator subsequently operating the foot pedal in accordance with the selected one displayed available mode within a portion of a surgical procedure.

31. The foot pedal of claim 30, wherein at least one of the directional movements of the treadle is capable of acting as a linear control.

32. The foot pedal of claim 30 wherein the foot pedal is used with a phacoemulsification system.

33. A method of programming a linear foot pedal, comprising:
  programming a selected directional movement of a treadle of the linear foot pedal using the linear foot pedal by positioning a treadle of the foot pedal at a first position for one operational setting and confirming the first position as the starting position of the one operational setting and positioning the treadle at a second position for another operational setting and confirming the second position as the starting position of the another operational setting, wherein confirming comprises one selected from the group consisting of clicking an icon on the display, pressing a switch on the foot pedal, moving the treadle, voicing a command, and combinations thereof, and programming movement in a perpendicular direction to the selected directional movement to function as a mode using the linear foot pedal; and subsequently operating the linear foot pedal in accordance with the operational settings within a portion of a surgical procedure;

wherein programming the selected directional movement further comprises a user toggling through candidate surgical settings displayed on a display using the foot pedal and selecting one displayed surgical setting.

34. The method of claim 33, wherein the foot pedal is used with a phacoemulsification system.

* * * * *